United States Patent [19]
Shin et al.

[11] Patent Number: 5,843,773
[45] Date of Patent: Dec. 1, 1998

[54] APOPTOSIS REGULATING GENE

[75] Inventors: Hee Sup Shin, Euwang; Young Chul Sung, Pohang; Seok Il Hong, Seoul; Sun Sim Choi, Soonchun; Jin Won Yun, Inchun; Eun Kyoung Choi, Kimchun; In Chul Park, Seoul, all of Rep. of Korea

[73] Assignees: Korea Green Cross Corporation; Postech Foundation, both of Rep. of Korea

[21] Appl. No.: 737,980

[22] PCT Filed: Mar. 25, 1996

[86] PCT No.: PCT/KR96/00040

§ 371 Date: Nov. 22, 1996

§ 102(e) Date: Nov. 22, 1996

[87] PCT Pub. No.: WO96/30513

PCT Pub. Date: Oct. 3, 1996

[30] Foreign Application Priority Data

Mar. 24, 1995 [KR] Rep. of Korea ..................... 1995/6266

[51] Int. Cl.⁶ .............................. C12N 15/11; C12N 5/00
[52] U.S. Cl. ....................... 435/320.1; 435/325; 536/23.1
[58] Field of Search ........................ 536/23.1; 435/320.1, 435/325

[56] References Cited

U.S. PATENT DOCUMENTS 4,889,806  12/1989  Olson et al. .......................... 435/172.3

OTHER PUBLICATIONS

Gillet G. Guerin, M, Trembleau A and Brun G. (1995), EMBO J., 14, 1372–1382.
Hague, A, Morghen M, Hicks D, Chapman M and Paraskeva C. (1994), Oncogene, 9, 3367–3370.
S. (McConkey DJ and Orrenus 1994), Trends in Cell Biol., 4, 370–374.
Nunez G and Clarke MF. (1994), Trends in Cell Biol., 4, 399–903.
Bissonnette RP, Echeverri F. Mahboubi A and Green GR. (1992), Nature, 359, 552–554.
Boise LH, Gonzalez–Garcia M, Postema CE, Ding L, Lindstein T. Turka LA Mao X, Nunez G and Thompson CB. (1993), Cell, 74, 597–608.
Castle VP, Heidelberger KP, Bromberg J. Ou X, Dole and Nunez G. (1993), Am. J. Pathol., 143, 1543–1550.
Choi SS, Yun JW, Choi EK, Cho YG, Sung YC and Shin HS. (1995), Mammalian Genome (in press).
Chittenden GI and Gulld BC. (1995), Nature, 374, 733–736.
Church G and Gilbert W. (1984), Proc. Natl. Aca.Sci. USA, 81, 1991–1995.
Clark AR, Purdie CA, Herrison DJ, Morris RG, Bird CC, Hopper ML and Wyllie AH.; (1993), Nature, 362, 849–852.
Farrow SN, White JHM, Martinou I, Raven T. Pun K–T, G rinham CJ, Martinous J–C and Brown R. (1995), Nature, 374, 731–733.
Fisher DE. (1994), Cell, 79, 539–542.
Garcia I, Martina I, Tsujimoto Y and Martiou J–C. (1992), Science, 258, 302–304.
Hengartner MO and Horvitz HR. (1994), Cell, 665–676.
Hockenbery D, Nunez G. Milliman C, Schreiber RD and Korsemeyer SJ. (1990), Nature, 348, 334–336.
Hockenbery D. Olrvail Z. Yin X–M, Milliman CL and Korsemeyer SJ. (1993), Cell, 75, 241–251.
Jacobson MD, Burne JF, King MP, Miyashita T. Reed JC and Raff MC. (1993), Nature, 361, 365–368.
Jacobson MD and Raff MC. (1995), Nature, 374, 814–816.
Kang H–M, St. Jacques B. Schwartz F and Shin H–S. (1994), Mol. Cells, 4, 27–32.
Kiefer MC, Brauer MJ, Powers VC, Wu JJ, Umansky SR, Tomel LD and Barr PJ. (1995), Nature, 374, 736–739.
Kozopas KM, Yabg T. Bunchan HL, Zhou P and Craig RW. (1993), Proc. Natl. Acad. Sci. USA, 90, 3516–3520.
Lin KY, Orlosfaky A, Berger MS and Prystowsky MB. (1993). J. Immunol., 151, 1979–1988.
Lowe SE, Schmit, EM, Smith SW, Osborne BA and Jacks T. (1993), Nature, 362, 847–849.
McDonnell TJ, Troncoso P. Brisbay SM, Logothetis C, Chung Look, Hsieh J–T, Tu S–M and Campbell ML. (1992), Cancer Res., 52, 6940–6944.
Morgenbesser SD, Williams BO, Jacks T and Dephinho RA. (1994), Nature, 371, 72–74.
Nunez G. London L, Hockenbery D, Alexander M, Mckearn JP and Korsemeyer SJ. (1990), J. Immunol., 144, 3602–3610.
Nunez G. Merino R. Grillot D and Gonzlez–Garcia M.(1994), Immunol . Today, 15, 582–587.
Oltvai ZN, Milliman CL and Korsmeyer SJ. (1993), Cell, 74, 609–619.
Osborne BA and Schwartz LM. (1994), Trends in Cell Biol., 4, 394–399.
Papadopoulos N. Nicolaides NC, Wei Y–F, Ruben SM, Carter KC, Rosen CA, Haseltaine WA, Fleischmann RD, Fraser CM, Adams MD, Venter JC, Hamilton SR Peterson GM, Watson P. Lynch HT, Peltomaki P. Mecklin JP, Chapelle A, Kinzler KW and Vogelstein B. (1994), Science, 263, 1625–1628.
Reed JC, Cuddy M, Slabiak T. Croce CM and Nowell PC. (1988), N.ature, 336, 259–261.
Sambrook J. Fritsch EF and Maniatis T. (1989), Molecular Cloning, 1, n7.3–n7.36.
Sentman CL, Shutter JR, Hockenbery D, Kanakawa O and Korsmeyer SJ. (1991), Cell, 67, 879–888.
Shimizu S. Eguchi Y. Kosaka H. Kamiike W. Matsuda H and Tsujimoto Y. (1995), Nature, 374, 811–813.
Strasser A, Harris AW and Cory S. (1991). Cell, 67, 889–899.

(List continued on next page.)

Primary Examiner—Lila Feisee
Assistant Examiner—Susan Ungar
Attorney, Agent, or Firm—McAulay Fisher Nissen Goldberg & Kiel, LLP

[57] ABSTRACT

A new Bcl-2 related gene "Bfl-1", a polypeptide encoded by said gene, and a plasmid and a transformant comprising said gene are disclosed. The gene can be used to detect cancer.

7 Claims, 5 Drawing Sheets

OTHER PUBLICATIONS

Strasser A. Harris AW, Bath ML and Cory S. (1990). Nature, 348, 331–333.

Thomson CB. (1995), Science, 267, 1456–1462.

Trauth BC, Klas C, Peters MJ, Mat zku S. Moller P. Falk W. Debatin K–M and Krammer PH. (1989), Science, 245, 301–304.

Tsujimoto T. Gorham J. Cossman J. Jaffe E and Corce CM.(1985), Science, 229, 1390–1393.

Vaux DL, Cory S and Adams JM. (1988), Nature, 335, 440–442.

Veis DJ, Sorenson CM, Shutter JR and Korsmeyer SJ. (1993), Cell, 75, 229–240.

Williams BO, Remington E, Albert DM, Mukai S. Bronson RT and Jacks T. (1994), Nature genes., 7, . 480–484.

Williams GT. (1991), Cell, 65, 1097–1098.

Williams GT and Smith CA. (1993), Cell, 74, 777–779.

Williams GT, Smith A, Spooncer E, Dexter TM and Taylor DR. (1990), Nature, 343, 76–79.

Sambrook et al (Molecular Cloning, A Laboratory Manual Cold Spring Harbor, 1989, pp. 16.3–16.4).

FIG. 1A

Bfl-1

CCAGCTCAAGACTTTGCTCTCCACCAGGCAGAAGATGACAGACTGTGAATTTGGATATATTTACNGGCTG
GCTCAGGACTATCTGCAGTGCNTCCTACAGATACCACAACCTGGATCAGGTCCAAGCAAAACGTCCAGAG
TGCTACAAAATNTTGCNTTCTCAGTCCAAA

FIG. 1B

| Sequences producing High-scoring Segment Pairs: | | Reading Frame | High Score | Smallest Poisson Probability P(N) | N |
|---|---|---|---|---|---|
| L16462 | hemopoietic-specific early-response protein [Mu... | +2 | 105 | 5.8e-09 | 1 |
| M14917 | Influenza A/Ken/1/81 (H3N8), neuraminidase, RNA.. | −3 | 52 | 0.71 | 1 |
| M67463 | polyprotein [Hepatitis C virus] | +2 | 52 | 0.95 | 1 |
| X62743 | Mb gene product [Mus musculus] | +2 | 51 | 0.98 | 1 |
| M32084 | Hepatitis C virus polyprotein gene, partial CDs... | +2 | 51 | 0.99 | 1 |
| D10749 | polyprotein precursor [hepatitis C virus] | +2 | 51 | 0.99 | 1 |
| M62321 | HCV-1 [Hepatitis C virus] | +2 | 51 | 0.99 | 1 |
| X62936 | vlpa gene product [Mycoplasma hyorhinis] | −3 | 47 | 0.9995 | 1 |
| S39346 | gag homolog. pol homolog {non-LTR retrotranspos.... | −3 | 47 | 0.9998 | 1 |

```
>L16462  hemopoietic-specific early-response protein [Mus Musculus]
         Length = 172

Query:   35  MTDCEFGYIYXLAQDYLQCXLQIPQPGSGPSKTSRVLQNXAFSVQ          169
             M + E  +I+ LA+ YLQ LQ+P   S PS+  RVLQ  AFSVQ
Sbjct:    1  MAESELMHIHSLAEHYLQYVLQVPAFESAPSQACRVLQRVAFSVQ           45
```

FIG. 2A

```
Bfl-1   MTDCEFGYIYRLAQDYLQCVLQIPQPGSGPSKTSRVLQNVAFSVQKEVEKNLKSCLDNVNV   61
        M + E  +I+ LA+ YLQ VLQ+P   S PS+   RVLQ VAFSVQKEVEKNLKS LD+ +V
        MAESELMHIHSLAEHYLQYVLQVPAFESAPSQACRVLQRVAFSVQKEVEKNLKSYLDDFHV   61
```

FIG. 2B

```
Bfl-1   VSVDTARTLFNQVMEKEFEDGIINWGRIVTIFAFEGILIKKLLRQQIAPDVDTYKEISYFV   118
        S+DTAR +FNQVMEKEFEDGIINWGRIVTIFAF G L+KKL ++QIA DV  YK++S FV
   a1   ESIDTARIIFNQVMEKEFEDGIINWGRIVTIFAFGGVLLKKLPQEQIALDVCAYKQVSSFV   122
```

FIG. 2C

```
Bfl-1   AEFIMNNTGEWIRQNGGWENGFVKKFEPKSGWMTFLEVTGKICEMLSLLKQYC         175
        AEFIMNNTGEWIRQNGGWE+GF+KKFEPKSGW+TFL++TG+I EML LLK
   A1   AEFIMNNTGEWIRQNGGWEDGFIKKFEPKSGWLTFLQMTGQIWEMLFLLK            172
```

Comparison of Bfl-1 And Other Bcl-2-related Genes

FIG. 3A

```
Bcl-2                                         MAHAGRTGYDNREIVMKYIHYKLSQRGYEWDAGDV    35
 MCL1    ATPARLLFFAPTRRAAPLEEMEAPAADAIMSPEEELDGYEPEPLGKRPAVLPLLELVGESG   153
Bcl-x                                                MSQSNRELVVDFLSYKLSQKGYSWSQFS    28
  Bak                                                     MASGQGPGPPRQWCGE    16
```

FIG. 3B

```
Bfl-1                                         MTDCEFGYIYRLAQDYLQCVLQIPQPGSGPSKTSRVLQ    38
   A1                                         MAESELMHIHSLAEHYLQYVLQVPAFESAPSQACRVLQ    38
Bcl-2    GAAPPGAAPAPGIFSSQPGHTPHPAASRDPVARTSPLQTPAAPGAAAGPALSPVPPVVHLI    96
 MCL1    NNTSTDGSLPSTPPPAEEEEDELYRQSLEIISRYLREQATGAKDTKPMGRSGATSRKALET   214
Bcl-x    DVEENRTEAPEGTESEMETPSAINGNPSWHLADSPAVNGATGNSSSLDAREVIPMAAVKQA    89
  Bak    PALPSASEEQVAQDTEEVFRSYVFYRHQQEQEAEGVAAPADPEMVTLPLQPSSTMGQVGRQ    77
  Bax          MDGSGEQPRGGGPTSSEQIMKTGALLLQGFIQDRAGRMGGEAPELALDPVPQDASTKKL    59
NR-13                                MPGSLKEETALLLEDYFQHRAGGAALPPSATAAE    34
```

FIG. 3C

```
                                                       BH1
Bfl-1    NVAFSVQKEVEKNLKSCLDNVNVVSVD-TARTLFNQVMEKEFEDGIINWGRIVTIFAFEGI    99
   A1    RVAFSVQKEVEKNLKSYLDDFHVESID-TARIIFNQVMEKEFEDGIINWGRIVTIFAFGGV    99
Bcl-2    LRQAGDDFSRRYRGDFAEMSSQLHLTPFTARGRFATVVEELFRDGV-NWGRIVAFFEFGGV   156
 MCL1    LRRVGDGVQRNHETVFQGMLRKLDIKNEDDVKSLSRVMIHVFSDGVTNWGRIVTLISFGAF   273
Bcl-x    LREAGDEFELRYRRAFSDLTSQLHITPGTAYQSFEQVVNELFRDGV-NWGRIVAFFSFGGA   149
  Bak    LAIIGDDINRRYDSEFQTMLQHLQPTAENAYEYFTKIATSLFESGI-NWGRVVALLGFGYR   137
  Bax    -SECLKRIGDELDSNMELQRMIAAVDTDSPREVFFRMAADMFSDGNFNWGRVVALFYFASK   120
NR-13    LRRAAAELERRERPFERSCAPLARAEPREAAAILRKVAAQLEIDGGLNWGRLLALVVFAGT    95
```

FIG. 3D

```
                                 BH2
Bfl-1    LIKKLLRQQIAPDVDTYKEISYFVAEFIMNNTGEWIRQNGGWENGFVKKFEPKSGWMTFLE   160
   A1    LLKKLPQEQIALDVCAYKQVSSFVAEFIMNNTGEWIRQNGGWEDGFIKKFEPKSGWLTFLQ   160
Bcl-2    M---CVESVNREMSPLVDNIALWMTEYLNRHLHTWIQDNGGWDAFVELYGPSMRPLFDFSW   215
 MCL1    VAKHL---KTINQESCIEPLAESITDVLVRTKRDWLVKQRGWDGFVEFFHVEDLEGGIRNV   331
Bcl-x    L---CVESVDKEMQVLVSRIAAWMATYLNDHLEPWIQENGGWDTFVELYGNNAAAESRKGQ   208
  Bak    LALHV   YQHGLTGFLGQVTRFVVDFMLHHCIARWIAQRGGWVAALNLGNGPILNVLVVLG   196
  Bax    L---VLKALCTKVPELIRTIMGWTLDFLRERLLGWIQDQGGWDGLLSYFGTPTWQTVTIFV   165
NR-13    L---AAALAESACEEGPSRLAAALTAYLAEEQGEWMEEHGGWDGFCRFFGRHGSQPADQNS   153
```

FIG. 3E

```
Bfl-1    VTGKICEMLSLLKQYC             175
  A-1    MTGQIWEMLFLLK                172
Bcl-2    LSLKTLLSLALVGACITLGAYLSHK    239
 MCL1    LLAFAGVAGVGAGLAYLIR          350
Bcl-x    ERFNRWFLTGMTVAGVVLLGSLFSRK   233
  Bak    VVLLGQFVVRRFFKS              211
  Bax    AGVLTTASLTIWKKMG             193
NR-13    TLSNAIMAAAGFGIAGLAFLLVVR     177
```

NORTHERN BLOT ANALYSIS OF Bfl-1 GENE EXPRESSION IN SEVERAL HUMAN TISSUES AND CELL LINES

EXPRESSION Bfl-1 GENE IN STOMACH CANCER TISSUES

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 755 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( D ) DEVELOPMENTAL STAGE: Fetus at 22 weeks gestation
        ( F ) TISSUE TYPE: Liver ( i x ) FEATURE:
        ( A ) NAME/KEY: CDS
        ( B ) LOCATION:35..559

( i x ) FEATURE:
        ( A ) NAME/KEY: polyA_signal
        ( B ) LOCATION:713..718

( x i ) SEQUENCE DESCRIPTION: SEQ ID NO: 1:

```
CCAGCTCAAG  ACTTTGCTCT  CCACCAGGCA  GAAG ATG ACA GAC TGT GAA TTT            52
                                         Met Thr Asp Cys Glu Phe
                                         1               5

GGA TAT ATT TAC AGG CTG GCT CAG GAC TAT CTG CAG TGC GTC CTA CAG            100
Gly Tyr Ile Tyr Arg Leu Ala Gln Asp Tyr Leu Gln Cys Val Leu Gln
            10                  15                  20

ATA CCA CAA CCT GGA TCA GGT CCA AGC AAA ACG TCC AGA GTG CTA CAA            148
Ile Pro Gln Pro Gly Ser Gly Pro Ser Lys Thr Ser Arg Val Leu Gln
```

-continued

```
                       25                              30                              35
AAT  GTT  GCG  TTC  TCA  GTC  CAA  AAA  GAA  GTG  GAA  AAG  AAT  CTG  AAG  TCA       196
Asn  Val  Ala  Phe  Ser  Val  Gln  Lys  Glu  Val  Glu  Lys  Asn  Leu  Lys  Ser
     40                       45                       50

TGC  TTG  GAC  AAT  GTT  AAT  GTT  GTG  TCC  GTA  GAC  ACT  GCC  AGA  ACA  CTA       244
Cys  Leu  Asp  Asn  Val  Asn  Val  Val  Ser  Val  Asp  Thr  Ala  Arg  Thr  Leu
55                       60                       65                       70

TTC  AAC  CAA  GTG  ATG  GAA  AAG  GAG  TTT  GAA  GAC  GGC  ATC  ATT  AAC  TGG       292
Phe  Asn  Gln  Val  Met  Glu  Lys  Glu  Phe  Glu  Asp  Gly  Ile  Ile  Asn  Trp
               75                       80                            85

GGA  AGA  ATT  GTA  ACC  ATA  TTT  GCA  TTT  GAA  GGT  ATT  CTC  ATC  AAG  AAA       340
Gly  Arg  Ile  Val  Thr  Ile  Phe  Ala  Phe  Glu  Gly  Ile  Leu  Ile  Lys  Lys
               90                       95                      100

CTT  CTA  CGA  CAG  CAA  ATT  GCC  CCG  GAT  GTG  GAT  ACC  TAT  AAG  GAG  ATT       388
Leu  Leu  Arg  Gln  Gln  Ile  Ala  Pro  Asp  Val  Asp  Thr  Tyr  Lys  Glu  Ile
          105                      110                      115

TCA  TAT  TTT  GTT  GCG  GAG  TTC  ATA  ATG  AAT  AAC  ACA  GGA  GAA  TGG  ATA       436
Ser  Tyr  Phe  Val  Ala  Glu  Phe  Ile  Met  Asn  Asn  Thr  Gly  Glu  Trp  Ile
     120                      125                      130

AGG  CAA  AAC  GGA  GGC  TGG  GAA  AAT  GGC  TTT  GTA  AAG  AAG  TTT  GAA  CCT       484
Arg  Gln  Asn  Gly  Gly  Trp  Glu  Asn  Gly  Phe  Val  Lys  Lys  Phe  Glu  Pro
135                      140                      145                      150

AAA  TCT  GGC  TGG  ATG  ACT  TTT  CTA  GAA  GTT  ACA  GGA  AAG  ATC  TGT  GAA       532
Lys  Ser  Gly  Trp  Met  Thr  Phe  Leu  Glu  Val  Thr  Gly  Lys  Ile  Cys  Glu
                    155                      160                      165

ATG  CTA  TCT  CTC  CTG  AAG  CAA  TAC  TGT  TGACCAGAAA  GGACACTCCA                  579
Met  Leu  Ser  Leu  Leu  Lys  Gln  Tyr  Cys
               170                      175

TATTGTGAAA  CCGGCTAAT  TTTTCTGACT  GATATGGAAA  CGATTGCCAA  CACATACTTC                 639

TACTTTTAAA  TAAACAACTT  TGATGATGTA  ACTTGACCTT  CCAGAGTTAT  GGAAATTTTG                 699

TCCCCATGTA  ATGAATAAAT  TGTATGTATT  TTTCTCTAAA  AAAAAAAAAA  AAAAAA                    755
```

( 2 ) INFORMATION FOR SEQ ID NO: 2:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Thr  Asp  Cys  Glu  Phe  Gly  Tyr  Ile  Tyr  Arg  Leu  Ala  Gln  Asp  Tyr
 1                    5                        10                       15

Leu  Gln  Cys  Val  Leu  Gln  Ile  Pro  Gln  Pro  Gly  Ser  Gly  Pro  Ser  Lys
               20                       25                       30

Thr  Ser  Arg  Val  Leu  Gln  Asn  Val  Ala  Phe  Ser  Val  Gln  Lys  Glu  Val
          35                       40                       45

Glu  Lys  Asn  Leu  Lys  Ser  Cys  Leu  Asp  Asn  Val  Asn  Val  Val  Ser  Val
     50                       55                       60

Asp  Thr  Ala  Arg  Thr  Leu  Phe  Asn  Gln  Val  Met  Glu  Lys  Glu  Phe  Glu
65                       70                       75                       80

Asp  Gly  Ile  Ile  Asn  Trp  Gly  Arg  Ile  Val  Thr  Ile  Phe  Ala  Phe  Glu
               85                       90                       95

Gly  Ile  Leu  Ile  Lys  Lys  Leu  Leu  Arg  Gln  Gln  Ile  Ala  Pro  Asp  Val
              100                      105                      110

Asp  Thr  Tyr  Lys  Glu  Ile  Ser  Tyr  Phe  Val  Ala  Glu  Phe  Ile  Met  Asn
          115                      120                      125
```

-continued

| Asn | Thr | Gly | Glu | Trp | Ile | Arg | Gln | Asn | Gly | Gly | Trp | Glu | Asn | Gly | Phe |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |
| Val | Lys | Lys | Phe | Glu | Pro | Lys | Ser | Gly | Trp | Met | Thr | Phe | Leu | Glu | Val |
| 145 |     |     |     |     | 150 |     |     |     |     | 155 |     |     |     |     | 160 |
| Thr | Gly | Lys | Ile | Cys | Glu | Met | Leu | Ser | Leu | Leu | Lys | Gln | Tyr | Cys |     |
|     |     |     |     | 165 |     |     |     |     | 170 |     |     |     |     | 175 |     |

APOPTOSIS REGULATING GENE

BACKGROUND OF THE INVENTION

1. Field of the Invention

The present invention is related to a new apoptosis regulating gene, a plasmid containing the same, and a peptide encoded by the same.

Several publications are referenced in this application. Full citation to these references is found at the end of the specification immediately preceding the SEQUENCE LISTING or where the publication is mentioned.

2. Background of the Invention

Living cells are programmed to die spontaneously when they are useless. Such a programmed cell death is called "Apoptosis" and has widely attracted attentions in cell physiological fields.

Apoptosis plays an important role in many physiological processes, such as embryonic development, deletion of self-reactive T-cells (Williams, 1991; Williams and Smith, 1993), and in many diseases such as cancer or neurodegenerative disorders. Apoptosis also plays a critical role in maintaining homeostasis in many adult tissues. It is widely accepted that cell death and cell proliferation are precisely balanced to maintain the proper types of cells or tissues, and disruption of this balance can result in several pathological phenotypes (Williams, 1991).

Apoptosis is regulated by multiple factors, either the appearance of a stimulus such as glucocorticoid hormones for immature thymocyte (Trauth et al., 1989), or the disappearance of a stimulus such as IL-2 withdrawal from mature T lymphocyte (Duke and Cohen, 1986). Alternatively, apoptosis can also be induced by the removal of growth factors from hemopoietic lineage cells and neuronal cells (Williams et al., 1990; Garcia et al., 1992). It has been also that a number of signaling events, including cytosolic $Ca^{++}$ increase, cAMP accumulation, activation of protein kinase C and activation of protein tyrosine kinase, regulate apoptotic cell death (McCondey and Orrenus, 1994). Several genes regulating apoptosis in various tissues and circumstances were reported: P53 and Bcl-2 are two of the most studied regulatory genes.

Apoptosis is induced by inactivation of Rb in the lens (Morgenbesser et al., 1994; Williams et al., 1994) and by γ-irradiation in the lymphocytes (Clarke et al., 1993; Lowe et al., 1993), respectively in the presence of tumor suppressor p53. Overexpression of p53 can induce either growth arrest or apoptosis depending on the cell type, whereas loss of p53 function can produce resistance to apoptotic cell death, leading to aggressive tumors (Williams, 1994). Mutation of p53 is associated with the human malignancies, including lung, breast, colorectal, prostate and multiple hemopoietic tumors (Fisher, 1999), revealing a correlation between a perturbation of apoptosis and carcinogenesis.

Bcl-2 is homologous to the C. elegans ced-9 gene, an apoptosis-blocking gene (Hengartner and Horvitz, 1994), and is abundantly expressed in follicular lymphoma that is resulted from the t(14;18) chromosomal translocation (Tsujimoto et al., 1985). It has been known that deaths of a variety of cell types can be prevented by Bcl-2 overexpression, although not all forms of cell death are inhibited (Williams, 1991). Thymocyte overexpressing Bcl-2 were resistant to the induction of apoptosis by glucocorticoid, radiation or anti-CD3 treatments (Sentman et al., 1991; Strasser et al., 1991). Overexpression of Bcl-2 in B cell compartments increases the number of mature resting B cells (Strasser et al., 1991, due to extended cell survival rather than increases proliferation. The action mechanism of the Bcl-2 is not clear yet. Recently, Bcl-2 has been reported to protect apoptosis independent of the inhibition of reactive oxygen species (Jacobson and Raff, 1995; Shimize et al., 1995), which is contradictory to the previous results (Hockenbery et al., 1993).

Several genes with Bcl-2 related sequences have been reported. Bax, 21 kDa protein, was known to have 21% homology to Bcl-2, and inhibits the function of Bcl-2, perhaps by forming Bcl-2-Bax complex (Oltvai et al., 1993). Bcl-x was reported to have a high-level homology to Bcl-2 and like Bcl-2 prevents apoptotic cell death in IL3-dependent cells following growth factor deprivation (Boise et al., 1993). Bak was recently identified by yeast two-hybrid system, or polymerase chain reaction(PCR) using degenerate oligonucleotide primers corresponding to the most conserved domains among known Bcl-2 related genes, referred to as BH1 and BH2 (Chittenden and Gulld, 1995; Farrow et al., 1995; Kiefer et al., 1995). Bak was reported to bind to E1B 19K and the Bcl-xL and, like Bax, to induce apoptosis under certain conditions. NR-13 was activated by $p60^{v-src}$ and inhibited apoptosis in quail embryos (Gillet et al., 1995).

Al gene, a hemopoietic specific early response gene, has been reported to have a sequence homology with Bcl-2, and its expression is increased by the action of GM-CSF (Lin et al., 1993).

There are interesting reports that Bcl-2 cooperatively interacts with c-myc in tumorigenesis (Bissonnette et al., 1992; Fanidi et al., 1992). The overexpression of c-myc proto-oncogene implicated in cell transformation and cell-cycle progression also induces some forms of apoptosis. The discrepancy in the function of c-myc can be explained as a result of an interaction with other genes, including Bcl-2: Bcl-2 prevents apoptotic death of CHO cells, which induced by overexpression of c-myc. It has been also known that the elevated Bcl-2 expression is associated with androgen-independent prostate cancer (McDonnel et al., 1992). Recently, a new member of the Bcl-2 related genes, NR-13, had been reported to be activated by $p60^{v-src}$, non-receptor type tyrosine kinase in quail embryos (Gillet et al., 1995). These results indicate that oncogenesis can be induced by another mechanism, that is, failure of appropriate cell death rather than activation of cellular proliferation.

Under the circumstance that the mechanism of apoptosis at the molecular level is not understood, a finding of a new gene involved in the regulation of apoptosis can accelerate or help an understanding of the mechanism. The new gene can be used to develop a useful diagnostic agent or cancer therapy.

SUMMARY OF THE INVENTION

The present invention pertains to a new Bcl-2 related genes.

One object of the present invention is to provide Bfl-1 gene, a Bcl-2 related gene from a human fetal liver, comprising bases in SEQ ID NO:1 or equivalents thereof.

Other object of the present invention is to provide a plasmid containing the Bfl-1 gene.

Another object of the present invention is to provide a transformant bearing the plasmid.

Still another object of the present invention is to provide a polypeptide comprising amino acids 1–175 of SEQ ID NO:2.

BRIEF DESCRIPTION OF THE DRAWINGS

These and various other features and advantages of the present invention will be readily understood with reference to the following detailed description taken in conjunction with the accompanying drawings, in which:

FIG. 1A shows a partial base sequence of Bfl-1 gene determined by random sequencing, and FIG. 1B shows the results of computerized searches for various clones having homology in base sequence;

FIGS. 2A, 2B and 2C show a comparison of Bfl-1 gene and A1 gene at amino acid level;

FIGS. 3A through 3E show comparisons of Bfl-1 gene and other Bcl-2 related genes in amino acid level;

FIG. 4A shows expression patterns of Bfl-1 gene in 24 week old human fetal liver, adult normal liver, hepatic tumor, nontumor liver tissue from the hepatoma patient, bone marrow, hemopoietic lineage cell lines including HL60, H9, Raji and ALL(Acute myeloid leukemia). FIG. 4B shows expression patterns of Bfl-1 gene in normal human tissues including kidney, lung, spleen, esophagus, testis, thyroid, heart, cerebellum, cerebrum. Lanes are labeled with the names of the corresponding tissues and cell lines. Photograph of the corresponding ethidium bromide-stained gel is shown below autoradiogram.

FIG. 5 is expression of Bfl-1 gene in stomach cancer tissues.

DETAILED DESCRIPTION OF THE INVENTION

Figure 4A:
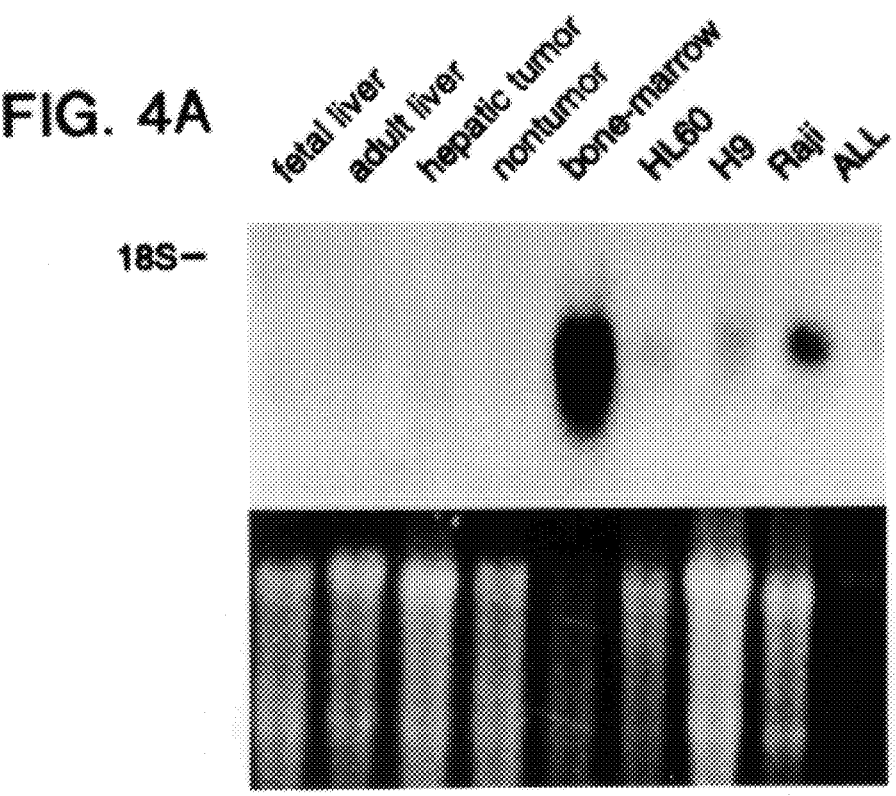
FIGS. 4A and 4B are Northern blot analysis of Bfl-1 gene expression in several human tissues and cell lines. Northern blots were prepared by loading 20–30 pg per lane of total RNA isolated from various tissues and cell lines.

The new gene according to the present invention was originally isolated from a human fetal liver at 22 week of gestation and identified by computer analysis of expressed sequenced tag (EST) databases constructed by single-pass sequencing of random cDNA clones (Choi et al., 1995).

A directional cDNA library was constructed from total RNA from a 22 week old human fetal liver, and used for its amplification by using competent cells. The DNAs were sequenced and each clone was identified. Among the sequenced clones, a clone showing a homology with murine A1 gene was selected and designated as "fl-383d." The fl-383d clone proved to be a new member of the Bcl-2 related gene family, and the new Bcl-2 related gene was named "Bfl-1" ("Bcl-2 related gene expressed in fetal liver").

Bfl-1 gene has a homology with Bcl-2, especially within the BH1 and BH2 domains. Bcl-2 has been shown to prevent apoptotic cell death in cultured cells deprived of growth factors (Vaus et al., 1988;

Hockenbery et al., 1990; Nunez et al., 1990; Garcia et al., 1992). Bcl-2, however, is not able to block apoptosis in all cells induced by cytokine deprivation or receptor-mediated signaling in vivo or in vitro (Nunez et al., 1990; Strasser et al., 1991). These facts suggest the existence of multiple intracellular pathways of apoptosis, each requiring several independent gene products. Since only some pathways can be prevented by Bcl-2, there have been efforts to find a new member of Bcl-2 related gene family or polypeptides that interact with Bcl-2. Some gene products whose sequences are similar to Bcl-2 have been reported including Bax, Bcl-x, MCL1, A1, Bak and NR-13.

The homology among the Bcl-2 related proteins is concentrated in two regions, termed BH1 and BH2 (Oltvai et al., 1993). The BH1 and BH2 domains are likely to play an important role in regulation of apoptosis, perhaps by modulating the activity of Bcl-2. Bcl-x isolated by low stringency hybridization to the Bcl-2 probe has two transcripts of different sizes generated by alternative splicing. Overexpression of Bcl-xL containing BH1 and BH2 domains prevents apoptosis following growth factor deprivation, whereas Bcl-xSS lacking the internal region of. 63 amino acids corresponding to BH1 and BH2 facilitates apoptosis by inhibiting the activity of Bcl-2 (Boise et al., 1993).

Bax was identified by coimmunoprecipitation with Bcl-2, perhaps due to interaction within BH1 and BH2 domains, and appeared to inhibit the function of Bcl-2 by forming heterodimers, Bcl-2-Bax complexes (Oltvai et al., 1993).

Accordingly, the fact that Blf-1 contains BH1 and BH2 domains strongly suggests that the gene may also be involved in the regulation of apoptosis.

The Bfl-1 gene is highly expressed in bone marrow and present in hemopoietic lineages such as Raji and HL60 and in some normal adult tissues, including lung, spleen, and esophagus. The expression patterns of other Bcl-2 related genes are very distinctive. Bcl-2 is expressed in bone marrow progenitors or long-lived cells in hormonally responsive epithelia that undergo cycles of hyperplasis and in neurons of the peripheral neuronal system (Veis et al., 1993). Bcl-x is highly expressed in the thymus and the central nervous system (Boise et al., 1993). Bax expression was not lymphoid restricted but was widely expressed in a variety of tissues, including lung, stomach, kidney, thymus, bone marrow and spleen (Oltvai et al., 1993). Like Bax, Bak is ubiquitously expressed. A1 is a hemopoietic-specific gene expressed in several hemopoietic cell lineages (Lin et al., 1993). It is notable that the expression of apoptosis-accelerating genes such as Bax and Bak is widespread in different tissues, whereas the expression of apoptosis-blocking genes such as Bcl-2, Bcl-x and A1 is restricted in some tissues, suggesting that the activity of apoptosis-accelerating genes may be regulated by death inhibitory genes.

Figure 5A:
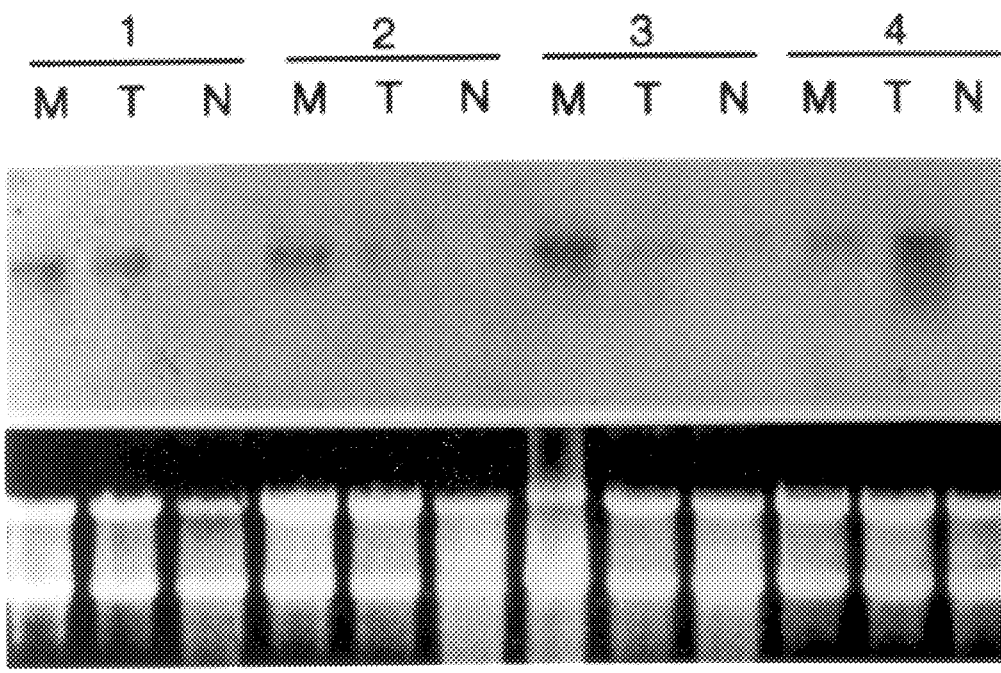
FIGS. 5A and 5B each show four sets of stomach tissues which were obtained from eight different stomach cancer patients. Each set consisted of a normal stomach, tumor tissue and metastatic tumor nodule. Photograph of the corresponding ethidium bromide-stained gel is shown below each autoradiogram. M: metastatic nodule, T:tumor tissue, N: normal stomach tissue.
Figure 5B:
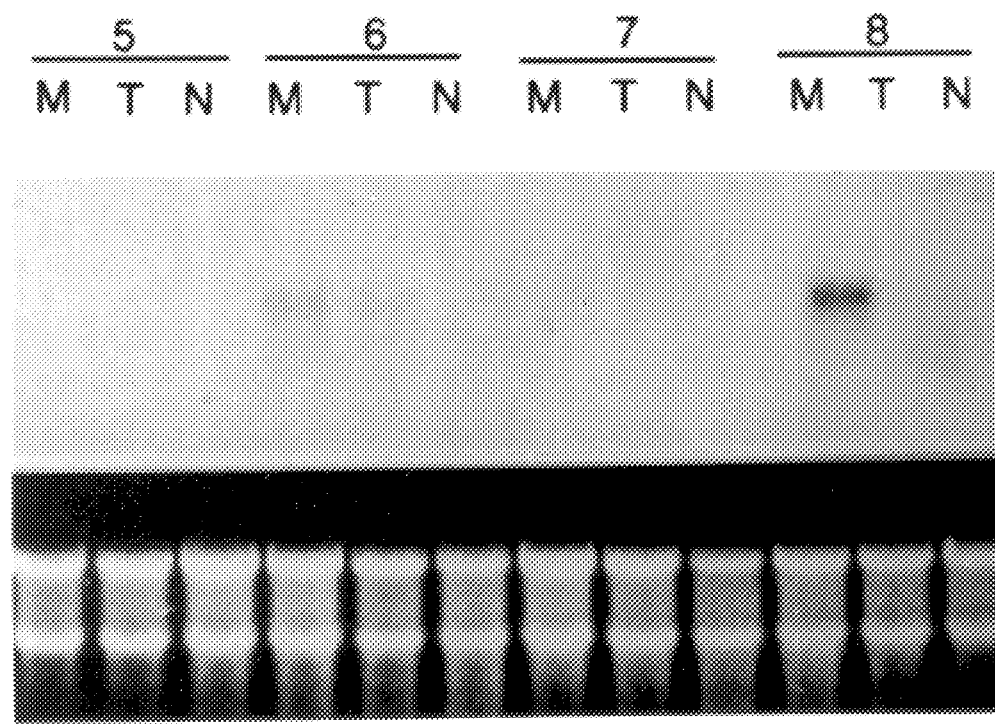

Interestingly, the expression of Bfl-1 appears to be correlated with the development of stomach cancer as shown in FIG. 5, suggesting the possibility that Bfl-1 may be involved in the tumorigenesis or progression of stomach cancer. This is in confirmation with the observation that the expression of Bcl-2 is prevalent in human colorectal adenomas and carcinomas (Hague et al., 1994) and the Bcl-2 expression has been associated with a poor prognosis in prostate cancer, colon cancer and neuroblastoma (McDonnel et al., 1992; Castle et al, 1993; Hague et al., 1994; Thomson, 1995). It is held that most human cancers result from the accumulation of several genetic changes, including activating mutations in proto-oncogenes and loss-of-function mutations in tumor suppressor genes. It has recently been suggested that the failure of appropriate cell death also contribute to tumorigenesis (Williams, 1991). It is conceivable that Bfl-1 may be involved in stomach cancer development or progression by promoting cell survival.

Bfl-1 is most homologous to A1 in the amino acid level and has a similar expression pattern, Bfl-1 may be the human homolog of the mouse A1 gene.

It is notable that the Bfl-1 gene was identified by random cDNA sequencing followed by computer analysis, suggesting that some human counterparts of the genes that have an important function in lower organisms but have not yet found in human might be already identified in exiting EST databases. A precedent to this result was the identification of the gene involved in hereditary nonpolyposis colon cancer (Papadopoulous et al., 1994).

The present invention also provides equivalent DNA constructs that encode various additions or substitutions of amino acid residues or sequences, or deletions of terminal or internal residues or sequences not needed for biological activity of the polypeptide comprising the amino acids 1–175 of SEQ ID NO:2.

Nucleic acid sequences within the scope of the invention include isolated DNA and RNA sequences that hybridize to the cDNA nucleotide sequences disclosed herein under conditions of moderate or severe stringency, which encode the polypeptide comprising the amino acids 1–175 of SEQ ID NO:2. Conditions of moderate stringency, as defined by Sambrook et al., Molecular Cloning : A Laboratory Manual, 2nd ed, Vol. 1, pp.1.101–1.104, Cold Spring Harbor Laboratory Press, (1989), include use of a prewashing solution of 5× SSC, 1.0 mM EDTA (pH 8.0) and hybridization conditions of about 55° C., 5× SSC, overnight. Conditions of severe stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that shown in SEQ ID NO:1 and still encode the polypeptide having the amino acid sequence of SEQ ID NO:2.

EXAMPLES

Materials and Methods

1. Isolation of RNA and cDNA library construction Total RNA was isolated from a 22 week old human fetal liver using guanidine thiocyanate protocol (Sambrook et al., 1989). Poly(A)$^+$ RNA was obtained from total RNA by oligo (dT)-cellulose chromatography. A directional cDNA library was constructed by using the cDNA synthesis kit purchased from Stratagene. Briefly, the first strand cDNAs were synthesized using moloney murine leukemia virus reverse transcriptase from 4 $\mu$g of poly(A)$^+$ RNA using a primer consisting of a XhoI site followed by oligo(dT). After second strand cDNA synthesis, EcoRI adaptors were ligated to both ends of the cDNAs, and then generated cDNAs were digested with XhoI. The digested cDNAs were loaded onto sephacryl spun column to select small fragments. Finally, the small fragments were ligated into EcoRI-XhoI site of pBluescript II SK(−) vector (available from Stratagene).

2. Single-pass sequencing and computer analysis

The cDNAs of constructed library were transfected into XL1-blue MRF' competent cells purchased from Stratagene. Double-stranded plasmid DNAs were prepared using alkaline lysis protocols, and sequenced by dideoxy-chain termination method following the manufacturer's recommendation (USB Biochemicals). That is to say, denatured templates were primed with T3 primer, labeled with $^{35}$S-dATP, and terminated. After reaction, samples were run in a 4.5% polyacrylamide gel. The gel was soaked in a solution consisting of 10% of methanol and 10% of acetic acid for 15 to 30 min, dried, and exposed to an X-ray film at room temperature for 12 to 14 hours.

Comparison between the generated sequences and public databases (Genbank, SWISS-PORT and PIR) was performed using BLAST program. The multiple sequence alignment was performed using the software package IG suite (IntelliGenetics Co, Mountain View, Calif.), installed on a SUN SPARC Staion 2 computer (SUN Microsystems, Inc, Mountain View, Calif).

3. Northern analysis

Total RNA of tissues and cell lines was isolated using guanidine thiocyanate protocol (Sambrook et al., 1989). About 20–30 $\mu$g of total RNA was loaded per lane of 1% denaturing formaldehyde-agarose gel and run at 40V for 16 hours. The RNA was transferred to a nylon membrane (Schleicher and Schuell) using 10× SSC. Radioactivity labeled probes (2×10$^5$ c.p.m. per ml) were hybridized to the blots at 65° C. in a buffer as described by Church and Gilbert (1984). After 18 h hybridization, the filters were washed in a buffer containing 0.1× SSC, 0.1% SDS at 65° C. for 15 min. The autoradiogram was taken for 1–7 days (Kang et al., 1994).

Results

1. Identification of a novel gene related to Bcl-2 from a fetal liver cDNA library Several novel genes were identified during the random cDNA sequencing project and one of those genes showed about 51% amino acid identity to the A1 gene in a stretch of 45 amino acid residues (P<0.01). The present inventors designated the newly found clone as "fl-383d." The fl-383d clone was ligated into the EcoRI-XhoI site of pBluescript II SK(−) (available from Stratagene) to produce a recombinant plasmid pBfl-1. Then the plasmid pBfl-1 was transformed into E. coli and designated as "383-E. coli". The transformant was deposited with Korean Culture Collection of Microorganisms (Korean Foundation of Culture Collection) of Department of Food Engineering, College of Engineering, Yonsei University, Sodaemun-gu, Seoul 120-749 Korea on Mar. 20, 1995 under the Budapest Treaty on the International Recognition of the Deposit of Microorganisms for the Purposes of Patent Procedure, and received an accession number "KCCM 10061."

FIG. 1(A) shows the partial base sequence of Bfl-1 gene determined by random cDNA sequencing, and FIG. 1(B) shows the results of evaluating the amino acid homology with other polypeptides stored in Genbank databases. In FIG. 1(B), the term "reading frame" means a frame used for the translation of base sequence, and the term "high score smallest poisson probability" is a computerized value by a sequence search program "BLAST (Basic Local Alignment Sequence Search Tool)." The score of "+5" is given when the amino acids compared are the same, while the score of "−4" is given when the amino acids compared are the different from each other. Therefore, the higher the score, the more homologous the amino acid sequences. The "p-value" also is a computerized value and indicates the possibility of an accidental match. Accordingly, the lower the value, the more specific the match.

The results of amino acid homology evaluation reveals that the Bfl-1 products shows the highest homology with the polypeptide L16462, an A1 gene product.

The detailed comparison of amino acids of the Bfl-1 and A1 products are shown in FIG. 2. As can be seen from FIG. 2, Bfl-1 gene shows similarity throughout the partially sequenced bases from its first amino acid, Met. The size of cDNA insert is about 750 bp, which is similar to that of A1 transcript.

The new Bcl-2 related gene according to the present invention is now named "Bfl-1 (Bcl-2 related gene expressed in fetal liver)."

The A1 gene is a Bcl-2 related gene in the mouse and is known as a hemopoietic specific dearly response gene whose transcription is rapidly and transiently induced by GM-CSF in murine bone marrow-derived macrophage (Lin et al., 1993). Since the Bcl-2 related genes play an important role in the regulation of apoptosis, the present inventors have determined the full DNA sequence of the novel cDNA gene and deduced the amino acid sequence of a potential open reading frame (SEQ ID NO:1). Bfl-1 is consisted of 734 bp and Kozak consensus sequence ("A" and "G" at −3 and −4 positions. A purine nucleotide, adenine, is located at −3 position from the putative translation initiation codon, ATG, which is preceded by an inframe stop codon, TGA indicating that the initiation codon seems to be a functioning one. The entire open reading frame from this start codon can potentially encode a protein of 175 amino acids, and a potential polyadenylation signal, AATAAA, was located in 18 base pairs upstream of the poly(A) tail. In SEQ ID NO. 1, in which full nucleotide sequence and deduced amino acid sequence of Bfl-1 is shown, the putative start codon, ATG, initiates the coding region which is translated into the three-letter code for the amino acid.

Comparison of the deduced amino acid sequence of the gene Bfl-1 with several Bcl-2 related genes including Bcl-2, Bax, Bcl-x, MCL1, A1, NR-13 and Bak was shown in FIG. 3. The deduced amino acid sequence of the Bfl-1 clone is aligned with several Bcl-2 related genes using alignment program (IntelliGenetic software package). The numbers in the right side indicate the positions of the amino acid in each sequence. Identical residues are indicated with bold face. The position where five or more proteins share the same residue are boxed. The BH1 and BH2 domains are marked by bold line. Among these Bcl-2 related genes, the gene Bfl-1 had the highest homology to the mouse A1 with a 72% amino acid identity. The overall degree of sequence identity between gene Bfl-1 and other Bcl-2 related genes was not very high except in the BH1 and BH2 domains, which have been known to be important for Bcl-2 function, indicating that the human cDNA clone fl-383d represents a new member of the Bcl-2 related gene family.

Figure 4B:
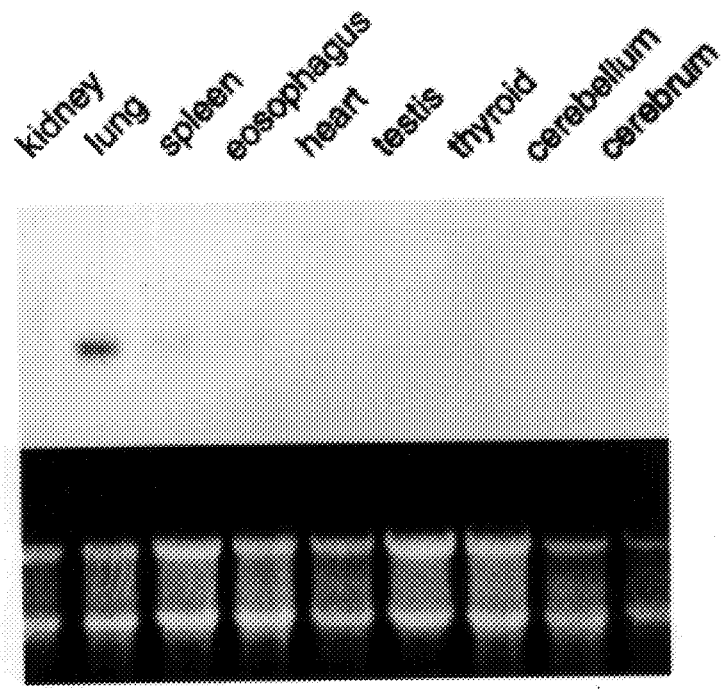

2. The Bfl-1 gene is abundantly expressed in bone marrow and at a low level in some other tissues To examine the expression pattern of Bfl-1, northern blot analysis was performed on various human tissues and cell lines (FIG. 5). Because Bfl-1 was initially identified from a human fetal liver at 22 weeks of gestation, which consists of hepatic and hemopoietic cells, the present inventors performed northern analysis of fetal liver, hemopoietic lineage cells such as HL60 and Raji, and primary acute lymphocyte leukemia (ALL) cells. The results are shown in FIG. 4. Bfl-1 was highly expressed in bone marrow, but not detected in fetal liver, indicating that the level of Bfl-1 expression is not high in the fetal liver (FIG. 4A). The Raji cell line derived from Burkitt's lymphoma expressed Bfl-1, whereas the other cell lines did not express Bfl-1, or did very little, if any. On northern analysis with various normal adult tissues, Bfl-1 message was detected at low levels in lung, spleen, and esophagus (FIG. 4B). No Bfl-1 message was detected in several other nonhemopoietic tissues including heart, testis, thyroid, cerebellum and cerebrum.

3. The expression of Bfl-1 is activated in stomach Cancer

It was reported that some of the Bcl-2 related genes may be involved in tumor cell survival (McDonnell et al., 1992; Thomson, 1995). Thus, the present inventors examined whether the expression of Bfl-1 is correlated with tumorigenesis. They analyzed tumor tissues for the expression of Bfl-1 by northern analysis. No correlation was observed in one set of hepatoma tissue (FIG. 4A). They then examined whether the expression of Bfl-1 is correlated with stomach cancer development. Northern analysis was carried out with eight sets of stomach tissue samples obtained from eight different stomach cancer patients (FIG. 5). Each set consisted of metastatic, tumorous, and normal stomach tissues from a single patient. In six out of the eight sets, the expression level of the gene was dramatically increased in tumorous and metastatic tissues, whereas normal stomach did not express the gene at a detectable level under the experimental conditions used. No apparent pathological or clinical difference was noted among the cancer samples, however, which could be correlated with the presence or the absence of the Bfl-1 expression.

REFERENCES

1. Bissonnette R. P., Echeverri F., Mahboubi A. and Green G. R. (1992), Nature, 359, 552–554
2. Boise L. H., Gonzalez-Garcia M., Postema C. E., Ding L., Lindstein T., Turka L. A., Mao X., Nunez G. and Thompson C. B. (1993), Cell, 74, 597–608
3. Castle V. P., Heidelberger K. P., Bromberg J., Ou X., Dole M. and Nunez G. (1993), Am. J. Pathol., 143, 1543–1550.
4. Choi S. S., Yun J. W., Choi E. K., Cho Y. G., Sung Y. C. and Shin H. S. (1995), Mammalian Genome (in press).
5. Chittenden G. I. and Gulld B. C. (1995), Nature, 374, 733–736
6. Church G. and Gilbert W. (1984), Proc. Natl. Aca. Sci. USA, 81, 1991–1995.
7. Clark A. R., Purdie C. A., Herrison D. J., Morris R. G., Bird C. C., Hooper M. L. and Wyllie A. H. (1993), Nature, 362, 849–852
9. Fanidi A., Harrington E. A. and Evan G. (1992), Nature, 359, 554–556.
10. Farrow S. N., White J. H. M., Martinou I., Raven T., Pun K.-T., Grinham C. J., Martinous J.-C. and Brown R. (1995), Nature, 374, 731–733.
11. Fisher D. E. (1994), Cell, 79, 539–542.
13. Garcia I., Martina I., Tsujimoto Y. and Martiou J.-C. (1992), Science, 258, 302–304.
14. Gillet G., Guerin M., Trembleau A. and Brun G. (1995), EMBO J., 14, 1372–1382.
15. Hague A., Morghen M., Hicks D., Chapman M. and Paraskeva C. (1994), Oncogene, 9, 3367–3370.
16. Hengartner M. O. and Horvitz H. R. (1994), Cell, 665–676.
17. Hockenbery D., Nunez G., Milliman C., Schreiber R. D. and Korsemeyer S. J. (1990), Nature, 348, 334–336.
18. Hockenbery D., Olrvail Z., Yin X.-M., Milliman C. L. and Korsemeyer S. J. (1993), Cell, 75, 241–251.
19. Jacobson M. D., Burne J. F., King M. P., Miyashita T., Reed J. C. and Raff M. C. (1993), Nature, 361, 365–368.
20. Jacobson M. D. and Raff M. C. (1995), Nature, 374, 814–816.
21. Kang H.-M., St. Jacques B., Schwartz F. and Shin H.-S. (1994), Mol. Cells, 4, 27–32.
22. Kiefer M. C., Brauer M. J., Powers V. C., Wu J. J., Umansky S. R., Tomel L. D. and Barr P. J. (1995), Nature, 374, 736–739.
23. Kozopas K. M., Yabg T., Bunchan H. L., Zhou P. and Craig R. W. (1993), Proc. Natl. Acad. Sci. USA, 90, 3516–3520.
24. Lin E. Y., Orlosfsky A., Berger M. S. and Prystowsky M. B. (1993). J. Immunol., 151, 1979–1988.
25. Lowe S. E., Schmit E. M., Smith S. W., Osborne B. A. and Jacks T. (1993), Nature, 362, 847–849.
26. McConkey D. J. and Orrenus S. (1994), Trends in Cell Biol., 4, 370–374.

27. McDonnell T. J., Troncoso P., Brisbay S. M., Logothetis C., Chung L. W. K., Hsieh J.-T., Tu S.-M. and Campbell M. L. (1992), *Cancer Res.,* 52, 6940–6944.
28. Morgenbesser S. D., Williams B. O., Jacks T. and Dephinho R. A. (1994), *Nature,* 371, 72–74.
29. Nunez G. and Clarke M. F. (1994), *Trends in Cell Biol.,* 4, 399–403.
30. Nunez G., London L., Hockenbery D., Alexander M., Mckearn J. P. and Korsemeyer S. J. (1990), *Immunol.,* 144, 3602–3610.
31. Nunez G., Merino R., Grillot D. and Gonzlez-Garcia M. (1994), *Immunol. Today,* 15, 582–587.
32. Oltvai Z. N., Milliman C. L. and Korsmeyer S. J. (1993), *Cell,* 74, 609–619.
33. Osborne B. A. and Schwartz L. M. (1994), *Trends in Cell Biol.,* 4, 394–399.
34. Papadopoulous N., Nicolaides N. C., Wei Y.-F., Ruben S. M., Carter K. C., Rosen C. A., Haseltaine W. A., Fleischmann R. D., Fraser C. M., Adams M. D., Venter J. C., Hamilton S. R., Peterson G. M., Watson P., Lynch H. T., Peltomaki P., Mecklin J. P., Chapelle A., Kinzler K. W. and Vogelstein B. (1994), *Science,* 263, 1625–1628.
35. Reed J. C., Cuddy M., Slabiak T., Croce C. M. and Nowell P. C. (1988), *Nature,* 336, 259–261.
36. Sambrook J., Fritsch E. F. and Maniatis T. (1989), *Molecular Cloning,* 1, n.3–n.36.
37. Sentman C. L., Shutter J. R., Hockenbery D., Kanakawa O. and Korsmeyer S. J. (1991), *Cell,* 67, 879–888.
38. Shimizu S., Eguchi Y., Kosaka H., Kamiike W., Matsuda H. and Tsujimoto Y. (1995), *Nature,* 374, 811–813.
39. Strasser A., Harris A. W. and Cory S. (1991). *Cell,* 67, 889–899.
40. Strasser A. Harris A. W., Bath M. L. and Cory S. (1990). *Nature,* 348, 331–333.
41. Thomson C. B. (1995), *Science,* 267, 1456–1462.
42. Trauth B. C., Klas C., Peters M. J., Matzku S., Moller P., Falk W., Debatin K.-M. and Krammer P. H. (1989), *Science,* 245, 301–304.
43. Tsujimoto T. Gorham J., Cossman J., Jaffe E. and Corce C. M.(1985), *Science,* 229, 1390–1393.
44. Vaus D. L., Cory S. and Adams J. M. (1988), *Nature,* 335, 440–442.
45. Veis D. J., Sorenson C. M., Shutter J. R. and Korsmeyer S. J. (1993), *Cell,* 75, 229–240.
46. Williams B. O., Remington E., Albert D. M., Mukai S., Bronson R. T. and Jacks T. (1994), *Nature genet.,* 7, 480–484.
47. Williams G. T. (1991), *Cell,* 65, 1097–1098.
48. Williams G. T. and Smith C. A. (1993), *Cell,* 74, 777–779.
49. Williams G. T., Smith A., Spooncer E., Dexter T. M. and Taylor D. R. (1990), *Nature,* 343, 76–79.

---

We claim:

1. A gene comprising the DNA sequence of SEQ ID NO:1.
2. A gene according to claim 1, extracted from human.
3. A gene according to claim 1, extracted from human fetal liver.
4. A gene according to claim 1, which is Bfl-1 (KCCM 10061).
5. A gene according to claim 1 comprising DNA sequence 35–559 Of SEQ ID NO:1.
6. A plasmid comprising the gene of claim 1.
7. A host cell transformed with the plasmid of claim 7.

* * * * *